United States Patent
Fritzsche et al.

(10) Patent No.: US 7,820,865 B2
(45) Date of Patent: Oct. 26, 2010

(54) PHOTOLATENT SYSTEMS

(75) Inventors: Katharina Fritzsche, Weil am Rhein (DE); Walter Fischer, Reinach (CH); Johannes Benkhoff, Basel (CH); Karin Powell, Lörrach (DE); Dirk Simon, Lörrach-Brombach (DE)

(73) Assignee: Ciba Corporation, Tarrytown, NY (US)

( * ) Notice: Subject to any disclaimer, the term of this patent is extended or adjusted under 35 U.S.C. 154(b) by 82 days.

(21) Appl. No.: 12/084,335

(22) PCT Filed: Oct. 30, 2006

(86) PCT No.: PCT/EP2006/067912

§ 371 (c)(1),
(2), (4) Date: Apr. 29, 2008

(87) PCT Pub. No.: WO2007/054446

PCT Pub. Date: May 18, 2007

(65) Prior Publication Data

US 2009/0162307 A1    Jun. 25, 2009

(30) Foreign Application Priority Data

Nov. 9, 2005    (EP) ................... 05110539

(51) Int. Cl.
   *C07C 49/00*    (2006.01)
   *A61K 8/18*    (2006.01)
   *A61Q 5/02*    (2006.01)

(52) U.S. Cl. ............... 568/325; 568/329; 568/337; 424/65; 424/70.1; 510/119; 510/158

(58) Field of Classification Search ............ 568/325, 568/329, 337
   See application file for complete search history.

(56) References Cited

U.S. PATENT DOCUMENTS

| | | | |
|---|---|---|---|
| 3,461,164 A | 8/1969 | Schulte et al. | 260/570.6 |
| 4,695,581 A | 9/1987 | Suzuki et al. | 514/415 |
| 5,476,860 A | 12/1995 | Bernardon | 514/319 |

OTHER PUBLICATIONS

Saburi et al. Photolysis of omega-phenoxyacetophenone. HCAPLUS abstract; Accession No. 1973:404609, Document No. 79:4609; 1973.*
K. H. Klingler, Drug Research, vol. 27, No. 1, (1977), pp. 4-14.
R. S. Givens et al., J. Am. Chem. Soc., vol. 122, (2000), pp. 2687-2697.
K. Zhang et al., J. Am. Chem. Soc., vol. 121, (1999), pp. 5625-5632.
L. Schwartz et al., J. Org Chem., vol. 34, No. 5, May 1969, pp. 1499-1500.
A. Cooke et al., Bioorganic & Medicinal Chemistry Letters, vol. 11, (2001), pp. 927-930.
U. T. Bhalerao et al., Synthetic Communications, vol. 25, No. 10, (1995), pp. 1433-1439.

* cited by examiner

*Primary Examiner*—Sikarl A Witherspoon
(74) *Attorney, Agent, or Firm*—Tyler A. Stevenson

(57) ABSTRACT

The instant invention relates to new photolatent compounds of the formula I wherein $R_1$ and $R_2$ are each independently of the other $C_1$-$C_{10}$alkyl or $C_3$-$C_8$cycloalkyl, $R_3$ is hydrogen or $C_1$-$C_4$alkyl, and wherein the photochemically cleaved group $R_4$OH is selected from the group consisting of fragrances, UV absorbers, anti-microbials, anti-fogging agents and clarifiers; with the proviso that, when $R_1$ and $R_2$ are tert-butyl and $R_3$ is hydrogen, $R_4$ is not methyl or phenyl.

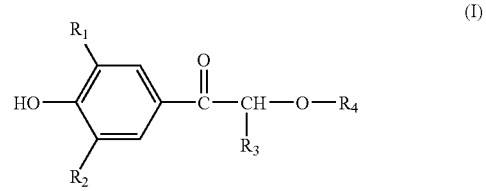

(I)

15 Claims, No Drawings

PHOTOLATENT SYSTEMS

The present invention relates to novel photolatent 4-hydroxy-phenacyl derivatives of effect molecules such as for example fragrances, UV absorbers, anti-microbials, anti-fogging agents or clarifiers, to compositions comprising a technical material, preferably a solvent, a wax, a film-forming binder, a paint, a coating, a natural or synthetic polymer, a fabric, a paper, a cleaner, a polish, a fabric care, a shampoo, a hair conditioner, a hair spray, a soap, a bath or shower gel or a body deodorant and the novel photolatent 4-hydroxy-phenacyl derivatives of effect molecules; as well as the use of the novel photolatent 4-hydroxy-phenacyl derivatives as precursors for the release of for example fragrances, UV absorbers, anti-microbials, anti-fogging agents and clarifiers with light.

State of the art for photolatent systems are 2-nitrobenzyl derivatives with or without further substitutents as protected intermediates as disclosed for example by Peter Wan et al., J. Am. Chem. Soc. 1999, 121, 5625-5632. However, the 2-nitrobenzyl protecting group has several drawbacks. Nitroaromatics are thermally unstable and may not be precessable at higher temperatures, for example when extruded in thermoplastic polymers such as for example polypropylene. Additionally, upon deprotection by light, the toxic and colored 2-nitroso-benzaldehyde is formed as side product, adding some undesired properties such as discoloration and toxicity to the substrate. A further disadvantage of the 2-nitrobenzyl protecting group is that the photoproduct absorbs in the same spectral region as the protected intermediate thus hampering the efficient deprotection by an internal filter effect.

It has now been found that new 4-hydroxy-phenacyl derivatives circumvents essentially all these drawbacks. The 4-hydroxy-phenacyl derivatives are thermally stable up to 220-260° C. The photoproducts which are 4-hydroxyphenyl acetic acid derivatives are by far less colored and less toxic. Additionally, the photoproducts absorb at shorter wavelength compared to the protected intermediate which results in a much smaller undesired filter effect.

The present invention therefore provides a photolatent compound of the formula I

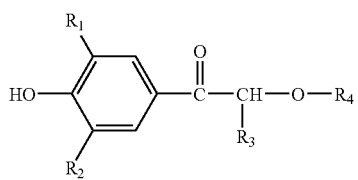

(I)

wherein $R_1$ and $R_2$ are each independently of the other $C_1$-$C_{10}$alkyl or $C_3$-$C_8$cycloalkyl, $R_3$ is hydrogen or $C_1$-$C_4$alkyl, and wherein the photochemically cleaved group $R_4OH$ is selected from the group consisting of fragrances, UV absorbers, anti-microbials, anti-fogging agents and clarifiers; with the proviso that, when $R_1$ and $R_2$ are tert-butyl and $R_3$ is hydrogen, $R_4$ is not methyl or phenyl.

Of interest are photolatent compounds of the formula I, wherein $R_1$ and $R_2$ are each independently of the other $C_1$-$C_{10}$alkyl or $C_3$-$C_8$cycloalkyl, $R_3$ is hydrogen or $C_1$-$C_4$alkyl, $R_4$ is unsubstituted $C_1$-$C_{25}$alkyl, $C_3$-$C_{25}$alkenyl, $C_3$-$C_{25}$alkinyl, $C_6$-$C_{10}$aryl, $C_3$-$C_{12}$cycloalkyl or $C_3$-$C_{12}$cycloalkenyl; or $C_1$-$C_{25}$alkyl, $C_3$-$C_{25}$alkenyl, $C_3$-$C_{25}$alkinyl, $C_6$-$C_{10}$aryl, $C_3$-$C_{12}$cycloalkyl and $C_3$-$C_{12}$cycloalkenyl substituted with $C_1$-$C_{18}$alkyl, $C_2$-$C_{18}$alkenyl, $C_3$-$C_{18}$alkinyl, $C_3$-$C_{12}$cycloalkyl, $C_1$-$C_{18}$alkoxy, hydroxyl, $C_2$-$C_{18}$alkoxycarbonyl, formyl, $C_1$-$C_{18}$alkylthio, $C_1$-$C_{18}$alkylsulfinyl, $C_1$-$C_{18}$alkylsulfonyl, halogen, carboxy, $C_2$-$C_{18}$-carboxyalkyl, $C_2$-$C_{18}$-carboxyalkoxy, $C_3$-$C_{18}$-alkoxycarbonylalkyl, $C_3$-$C_{18}$alkoxycarbonylalkoxy, $C_7$-$C_9$-phenylalkyl, phenoxy, halogen substituted phenoxy,

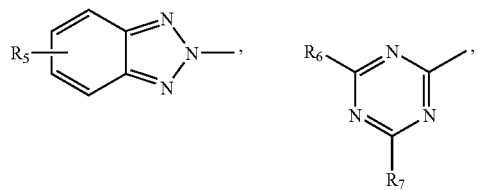

sorbityl or

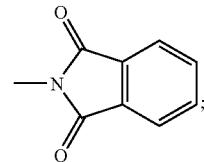

$R_5$ is hydrogen, $C_1$-$C_4$alkyl or halogen, and $R_6$ and $R_7$ independently of each other are phenyl or with $C_1$-$C_4$alkyl substituted phenyl; with the proviso that, when $R_1$ and $R_2$ are tert-butyl and $R_3$ is hydrogen, $R_4$ is not methyl or phenyl.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, octadecyl, icosyl or docosyl.

$C_3$-$C_{12}$Cycloalkyl is, for example, cyclopropyl, cyclobutyl, cyclopentyl, cyclohexyl, cycloheptyl, cyclooctyl, cyclononyl, cyclodecyl, cycloundecyl or cyclododecyl. Preference is given to cyclohexyl.

Alkenyl having 2 to 25 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl.

Alkinyl having 3 to 25 carbon atoms is a branched or unbranched radical such as, for example, propinyl, 2-butinyl, 3-butinyl, n-2,4-pentadiinyl, 3-methyl-2-butinyl, n-2-octinyl, n-2-dodecinyl, iso-dodecinyl, n-2-octadecinyl or n-4-octadecinyl.

$C_6$-$C_{10}$Aryl is for example phenyl or naphthyl.

$C_3$-$C_{12}$Cycloalkenyl is, for example, cyclopropenyl, cyclobutenyl, cyclopentenyl, cyclohexenyl, cycloheptenyl, cyclooctenyl, cyclononenyl, cyclodecenyl, cycloundecenyl or cyclododecenyl. Preference is given to cyclohexenyl.

Alkoxy having up to 18 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy.

$C_2$-$C_{18}$Alkoxycarbonyl is a branched or unbranched radical, for example methoxycarbonyl, ethoxycarbonyl, propoxycarbonyl, isopropoxycarbonyl, n-butoxycarbonyl, isobutoxycarbonyl, pentyloxycarbonyl, isopentyloxycarbonyl, hexyloxycarbonyl, heptyloxycarbonyl, octyloxycarbonyl, decyloxycarbonyl, tetradecyloxycarbonyl, hexadecyloxycarbonyl or octadecyloxycarbonyl.

Alkylthio having up to 18 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

Alkylsulfinyl having up to 18 carbon atoms is a branched or unbranched radical, for example methylsulfinyl, ethylsulfinyl, propylsulfinyl, isopropylsulfinyl, n-butylsulfinyl, isobutylsulfinyl, pentylsulfinyl, isopentylsulfinyl, hexylsulfinyl, heptylsulfinyl, octylsulfinyl, decylsulfinyl, tetradecylsulfinyl, hexadecylsulfinyl or octadecylsulfinyl.

Alkylsulfonyl having up to 18 carbon atoms is a branched or unbranched radical, for example methylsulfonyl, ethylsulfonyl, propylsulfonyl, isopropylsulfonyl, n-butylsulfonyl, isobutylsulfonyl, pentylsulfonyl, isopentylsulfonyl, hexylsulfonyl, heptylsulfonyl, octylsulfonyl, decylsulfonyl, tetradecylsulfonyl, hexadecylsulfonyl or octadecylsulfonyl.

Halogen substitutents will conveniently be chloro, bromo or iodo.

$C_2$-$C_{18}$-Carboxyalkyl is branched or unbranched radical, for example carboxymethyl, carboxyethyl, carboxypropyl, carboxybutyl, carboxypentyl, carboxyhexyl, carboxyheptyl, carboxyoctyl, carboxynonyl, carboxydecyl, carboxyundecyl, carboxydodecyl, carboxytetradecyl, carboxyhexadecyl or carboxyoctadecyl.

$C_2$-$C_{18}$-Carboxyalkoxy is branched or unbranched radical, for example carboxymethoxy, carboxyethoxy, carboxypropoxy, carboxybutoxy, carboxypentoxy, carboxyhexyloxy, carboxyheptyloxy, carboxyoctyloxy, carboxynonyloxy, carboxydecyloxy, carboxyundecyloxy, carboxydodecyloxy, carboxytetradecyloxy, carboxyhexadecyloxy or carboxyoctadecyloxy.

$C_3$-$C_{18}$-alkoxycarbonylalkyl is branched or unbranched radical, for example methoxycarbonylmethyl, methoxycarbonylethyl, ethoxycarbonylmethyl, propoxycarbonylethyl, ethoxycarbonylethyl, ethoxycarbonylpropyl, ethoxycarbonylbutyl, ethoxycarbonylpentyl, butoxycarbonylhexyl or butoxycarbonyldodecyl.

$C_3$-$C_{18}$-alkoxycarbonylalkoxy is branched or unbranched radical, for example methoxycarbonylmethoxy, methoxycarbonylethoxy, ethoxycarbonylmethoxy, propoxycarbonylethoxy, ethoxycarbonylethoxy, ethoxycarbonylpropoxy, ethoxycarbonylbutoxy, ethoxycarbonylpentoxy, butoxycarbonylhexoxy or butoxycarbonyldodecyloxy.

$C_7$-$C_9$-Phenylalkyl is, for example, benzyl, α-methylbenzyl, α,α-dimethylbenzyl or 2-phenylethyl.

Halogen substituted phenoxy, which contains preferably from 1 to 3, especially 1 or 2, halogens, is, for example, o-, m- or p-chlorophenoxy, or 2,4-dichlorophenoxy.

Of special interest are photolatent compounds of the formula I, wherein $R_1$ and $R_2$ are each independently of the other $C_3$-$C_8$alkyl or $C_5$-$C_8$cycloalkyl, $R_3$ is hydrogen or methyl, $R_4$ is unsubstituted $C_1$-$C_{18}$alkyl, $C_3$-$C_{18}$alkenyl, $C_3$-$C_{18}$alkinyl, $C_6$-$C_{10}$aryl, $C_5$-$C_8$cycloalkyl or $C_5$-$C_8$cycloalkenyl; or $C_1$-$C_{18}$alkyl, $C_3$-$C_{18}$alkenyl, $C_3$-$C_{18}$alkinyl, $C_6$-$C_{10}$aryl, $C_5$-$C_8$cycloalkyl and $C_5$-$C_8$cycloalkenyl substituted with $C_1$-$C_{12}$alkyl, $C_2$-$C_{12}$alkenyl, $C_3$-$C_{12}$alkinyl, $C_5$-$C_8$cycloalkyl, $C_1$-$C_{12}$alkoxy, hydroxyl, $C_2$-$C_{12}$alkoxycarbonyl, formyl, $C_1$-$C_{12}$alkylthio, $C_1$-$C_{12}$alkylsulfinyl, $C_1$-$C_{12}$alkylsulfonyl, halogen, carboxy, $C_2$-$C_{12}$-carboxyalkyl, $C_2$-$C_{12}$-carboxyalkoxy, $C_3$-$C_{12}$-alkoxycarbonylalkyl, $C_3$-$C_{12}$alkoxycarbonylalkoxy, $C_7$-$C_9$-phenylalkyl, phenoxy, halogen substituted phenoxy,

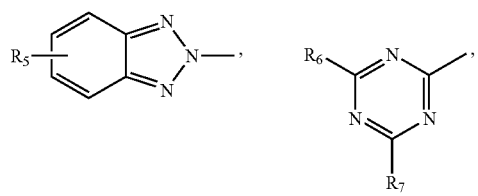

sorbityl or

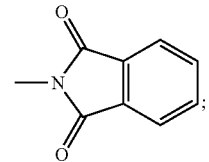

$R_5$ is hydrogen or halogen, and $R_6$ and $R_7$ are phenyl.

Of very special interest are photolatent compounds of the formula I, wherein $R_3$ is hydrogen.

Of interest are also photolatent compounds of the formula I, wherein $R_1$ and $R_2$ are each independently of the other $C_3$-$C_5$alkyl or cyclohexyl.

Preferred are photolatent compounds of the formula I, wherein $R_4$ is unsubstituted $C_2$-$C_{12}$alkyl, $C_3$-$C_{12}$alkenyl, $C_3$-$C_{12}$alkinyl, phenyl, cyclohexyl or cyclohexenyl; or $C_2$-$C_{12}$alkyl, $C_3$-$C_{12}$alkenyl, $C_3$-$C_{12}$alkinyl, phenyl, cyclohexyl and cyclohexenyl substituted with $C_1$-$C_4$alkyl, $C_2$-$C_8$alkenyl, $C_3$-$C_8$alkinyl, cyclohexyl, $C_1$-$C_8$alkoxy, formyl, chloro, carboxy, $C_7$-$C_9$-phenylalkyl, phenoxy, chloro substituted phenoxy,

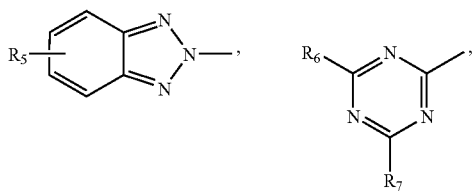

sorbityl or

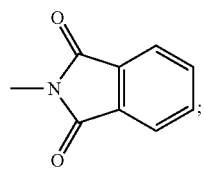

$R_5$ is hydrogen or chloro, and $R_6$ and $R_7$ are phenyl.

Also preferred are photolatent compounds of the formula I, wherein $R_1$ and $R_2$ are isopropyl, tert-butyl, cumyl or cyclohexyl.

Of very special interest are photolatent compounds of the formula I, wherein $R_1$ is $C_3$-$C_5$alkyl or cyclohexyl, $R_2$ is $C_3$-$C_5$alkyl or cyclohexyl, $R_3$ is hydrogen, $R_4$ is unsubstituted $C_2$-$C_{12}$alkyl, $C_3$-$C_{12}$alkenyl, $C_3$-$C_{12}$alkinyl, phenyl, cyclohexyl or cyclohexenyl; or $C_2$-$C_{12}$alkyl, $C_3$-$C_{12}$alkenyl, $C_3$-$C_{12}$alkinyl, phenyl, cyclohexy and cyclohexenyl substituted with $C_1$-$C_4$alkyl, $C_2$-$C_8$alkenyl, $C_3$-$C_8$alkinyl, cyclohexyl, $C_1$-$C_8$alkoxy, formyl, chloro, carboxy, $C_7$-$C_9$-phenylalkyl, phenoxy, chloro substituted phenoxy,

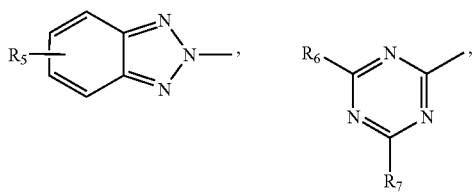

sorbityl or

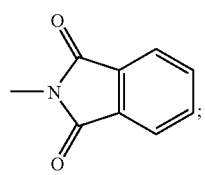

$R_5$ is hydrogen or chloro, and $R_6$ and $R_7$ are phenyl.

The photolatent compounds of the formula I can be prepared in per se known manner. In a typical reaction procedure, a compound of the formula Ia

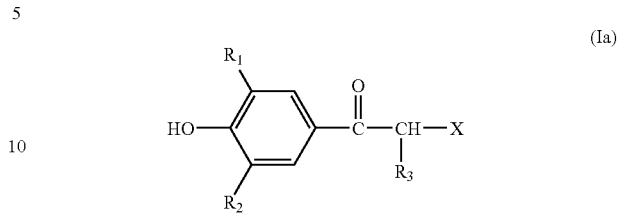

(Ia)

wherein $R_1$, $R_2$ and $R_3$ have the meaning as outlined above, and X is a leaving group such for example a halogen, is reacted with an alcohol $R_4$—OH, wherein $R_4$ has the meaning as outlined above, in the presence of a solvent and a base.

Bases of special interest are for example carbonates such for example potassium carbonate; hydroxides such for example sodium hydroxide or potassium hydroxide; or amines such for example tertiary amines, e.g. triethylamine; or pyridine.

Preferred solvents are for example protic or aprotic solvents such for example esters of carboxylic acids, e.g. ethyl acetate; ethers, e.g. diethyl ether or tetrahydrofuran; alcohols, e.g. methanol or ethanol; and dipolar aprotic solvents, e.g. dimethylformamide, N-methylpyrrolidone or acetonitrile.

The photolatent compounds of the formula I are suitable as precursors for the release of fragrances, UV absorber, anti-microbials, anti-fogging agents and clarifiers with light. In the context of the current invention fragrances include fragrances and flavours consciously and subconsciously perceptible by humans and animals by the sense of smell and taste including pheromones, attractants and repellents for insects, rodents and other pests and bait scents and blends thereof.

The photolatent compounds of the formula I can therefore be incorporated or added to any kind of technical material.

The present invention relates therefore also to compositions comprising a) a technical material, and b) at least a photolatent compound of the formula I.

Preferably, the technical material is for example a solvent, a wax, a film-forming binder, a paint, a coating, a natural or synthetic polymer, a fabric, a paper, a cleaner, a polish, a fabric care, a shampoo, a hair conditioner, a hair spray, a soap, a bath or shower gel or a body deodorant.

Illustrative examples of natural or synthetic polymers are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature.

b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends and alloys of the aforementioned polymers (polyblends), for example PP/EPDM, Polyamide/EPDM or ABS, PVC/EVA, PVC/ABS, PVC/MBS, PC/ABS, PC/Polyester, PBTP/-ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Particularly preferred technical materials are synthetic polymers, most preferably thermoplastic polymers and film-forming binders which are used in paints and coatings. Especially preferred technical materials are also rubbers and vulcanisates.

In another embodiment the technical material is a coating, an ink or adhesive. Examples of specific binders are:

Resins used in coatings are typically crosslinked polymers, for example, derived from aldehydes on the one hand and phenols, ureas and melamines on the other hand, such as phenol/formaldehyde resins, urea/formaldehyde resins and melamine/formaldehyde resins.

Also useful are unsaturated polyester resins derived from copolyesters of saturated and unsaturated dicarboxylic acids with polyhydric alcohols and vinyl compounds as crosslinking agents, and also halogen-containing modifications thereof of low flammability.

Preferably used are crosslinkable acrylic resins derived from substituted acrylates, for example epoxy acrylates, urethane acrylates or polyester acrylates.

Also possible are alkyd resins, polyester resins and acrylate resins crosslinked with melamine resins, urea resins, isocyanates, isocyanurates, polyisocyanates or epoxy resins.

Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

The coating material may also be a radiation curable composition containing ethylenically unsaturated monomers or oligomers and a polyunsaturated aliphatic oligomer.

The alkyd resin lacquers are conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99-123). Other crosslinking agents include glycouril resins, blocked isocyanates or epoxy resins.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the cross-linking agent for various acrylic or polyester resin systems that have been modified by the presence of reactive groups on the backbone structure.

When water-soluble, water miscible or water dispersible coatings are desired ammonium salts of acid groups present in the resin are formed. Powder coating composition can be pre-pared by reacting glycidyl methacrylate with selected alcohol components.

Aqueous coating materials can be based on water-soluble, water-thinnable polymers or polymer dispersions. Highly polar organic film formers, such as polyvinyl alcohols, polyacrylamides, polyethylene glycols, cellulose derivatives, acrylates and polyesters with very high acid value are examples for water-soluble polymers. Water-thinnable film formers consist of relatively short-chain polymers with acid or basic groups capable of salt formation incorporated into the side chains. They are neutralized with suitable bases or acids, which evaporates during film formation leads to insoluble polymers. Examples thereof are short and medium oil carboxylic acid alkyd resins, water-thinnable melamine resins, emulsifiable epoxy resins or silicone-based emulsions. Several polymer types are used as water-dilutable film formers. Most important of these are vinyl acetate copolymers with dibutyl maleinates, vinyl esters of Versatic acids, acrylic ester acids or terpolymers with ethylene and vinyl chloride, vinyl propionates, pure acrylates consisting of polyacrylates and polymethacrylates, acrylate copolymers with styrene and styrene-butadiene copolymers. Further aqueous binder systems are dispersions or emulsions of polyurethanes, including physically drying systems and systems carrying further crosslinkable groups. The coating material may also be a water-borne radiation-curable formulation of photopolymerisable compounds.

Adhesives are preferably selected from the group consisting of polyurethanes, polyacrylics, epoxys, phenolics, polyimides, poly(vinyl butyral), polycyanoacrylates, polyacrylates, ethylene/acrylic acid copolymers and their salts (ionomers), silicon polymers, poly(ethylene/vinyl acetate), atatic polypropylene, styrene-diene copolymers, polyamides, hydroxyl-terminated polybutadiene, polychloroprene, poly(vinyl acetate), carboxylated styrene/butadiene copolymers and poly(vinyl alcohol).

Aqueous emulsions of natural or synthetic rubber, are for example natural latex or latices of carboxylated styrene/butadiene copolymers.

The photolatent compounds of the formula I will preferably be added to the technical material to be treated in concentrations of 0.001 to 10%, preferably 0.01 to 10%, typically 0.1 to 5%, based on the weight of the technical material.

In addition to comprising the photolatent compounds of the formula I, the inventive compositions may comprise further additives, typically the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2, 2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3, 5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4- hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenyl propionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV absorbers and light stabilizers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethyl butyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(5'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethyl benzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyl-oxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$—]$_2$, where R=3'-tert-butyl-4'-hydroxy-5'-2H-benzotriazol-2-ylphenyl, 2-[2'-hydroxy-3'-(α,α-dimethyl benzyl)-5'-(1,1,3,3-tetramethylbutyl)-phenyl]-benzotriazole; 2-[2'-hydroxy-3'-(1,1,3,3-tetramethylbutyl)-5'-(α,α-dimethyl benzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-di-chloro-1,3,5-triazine, tris(2,2,6,6-tetramethyl-4-piperidyl)nitrilotriacetate, tetrakis(2,2,6,6-tetra-methyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethyl-piperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyl-oxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-tri-chloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro-[4,5]decane, a reaction product of 7,7,9,9-tetramethyl-2-cycloundecyl-1-oxa-3,8-diaza-4-oxo-spiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)-hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethyl-hexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4- dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydro-oxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyl-dibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Pigments and colorants depending on the kind of application organic as well as inorganic pigments are used as colorant. Examples for pigments are inorganic pigments, such as for example titanium dioxide, e.g. of the rutil or anatas type, zinc oxide, such as zinc white, zinc sulfide, barium sulfate, aluminium silicate, calcium silicate, carbon black, iron oxides, such as iron oxide yellow, iron oxide red, black iron oxide, iron blue, copper chromite black, chromium oxide greens, chrome green, violet (e.g. manganese violet, cobalt phosphate, $CoLiPO_4$), chromium yellow, chromium green, lead chromates, lead molybdates, cadmium titanate and pearlescent and metallic pigments, nickel titanium yellow, ultramarine blue, cobalt blue, bismuth vanadate, cadmium yellow or cadmium red; as well as organic pigments, such as monoazo pigments, di-azo pigments, di-azo condensation pigments, as well as metal complexes thereof, polycyclic pigments, such as perylene pigments, anthraquinone pigments, thioindigo pigments, or triphenylmethane pigments, as well as diketopyrrolo-pyrole pigments, isoindolinone pigments, e.g. tetrachlorisoindolinone pigments, isoindoline pigments, dioxazin pigments, benzimidazolone pigments and chinophthalone pigments, quinacridone pigments, dioxazine violet, vat pigments, and phthalocyanine pigments. Examples for suitable pigments include carbon black for a black coating, titanium dioxide for a white coating, diarylide yellow or diazo based pigments for yellow coatings, phthalocyanine blue, and other phthalocyanines for blue coatings, anthraquinone red, naphthole red, monazo based pigments, quinacridone pigments, anthraquinone and perylenes for red coatings, phthalocyanine green and nitroso based pigments for green coatings, monazo and diazo based pigments, quinacridone pigments, anthraquinones and perylenes for orange coatings, and quinacridone violet, basic dye pigments and carbazole dioxazine based pigments for violet coatings. The person skilled in the art is well aware of formulating and combining suitable further pigments if even more colored coatings, such as aqua, brown, gray, pink etc. are needed. Further examples of organic pigments can be found in the monograph: W. Herbst, K. Hunger "Industrielle Organische Pigmente" 2.sup.nd Edition, 1995, VCH Verlagsgesellschaft, ISBN: 3-527-28744-2.

14. Other additives, for example plasticisers, lubricants, emulsifiers, pigments, rheology additives, catalysts, flow-control agents, optical brighteners, flameproofing agents, antistatic agents and blowing agents.

15. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxy-ethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-di methylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctyl-benzofuran-2-one.

16. Photoinitiators, photocatalysts and photosensitizers, for example alpha-hydroxyketones (AHK), alpha-alkoxyketones(benzildimethylketals DBK) and alpha-aminoketones (AAK), benzophenones, mono- and bisacylphosphine oxides (BAPO), phenyl-glyoxylates, isopropyl-thioxanthone (ITX), oxime-esters, aminobenzoates, latent acids and bases and blends thereof. Other photoinitiators that can be used for this approach have been described in K. Dietliker, Photoinitiators for Free Radical, Cationic and Anionic Photopolymerization, Volume III in the series Chemistry and Technology of UV and EB Formulation for Coating, Inks and Paints, $2^{nd}$ Edition; John Wiley and Sons/SITA Technology Limited, New York/London 1998.

The further additives are typically used in concentrations of 0.01 to 10%, in case of fillers and colorants 0.01 to 60%, based on the total weight of the material to be treated.

The novel photolatent compounds of the formula I can be used in particular together with phenolic antioxidants, light stabilizers and/or processing stabilizers.

Incorporation of component (b) and, if desired, further additives into the synthetic polymers is carried out by known methods, for example before or during compounding, extrusion, co-extrusion or else by applying the dissolved or dispersed compounds to the synthetic polymer, if appropriate with subsequent slow evaporation of the solvent.

The present invention also relates to a composition in the form of a masterbatch or concentrate comprising component (a) in an amount of from 5 to 90% and component (b) in an amount of from 5 to 80% by weight.

Component (b) and, if desired, further additives, can also be added to the technical material before or during polymerisation or before crosslinking for example by dissolving the material directly in the technical material or in suitable solvent.

Component (b), with or without further additives, can be incorporated in pure form or encapsulated in waxes, oils or polymers into the synthetic polymer.

Component (b), with or without further additives, can also be sprayed onto the synthetic polymer. It is able to dilute other additives (for example the conventional additives indicated above) or their melts so that they too can be sprayed together with these additives onto the polymer. Addition by spraying on during the deactivation of the polymerization catalysts is particularly advantageous, it being possible to carry out spraying using, for example, the steam used for deactivation.

In the case of spherically polymerized polyolefins it may, for example, be advantageous to apply component (b), with or without other additives, by spraying.

The synthetic polymers prepared in this way can be employed in a wide variety of forms, for example as foams, films, fibres, tapes, moulding compositions, as profiles or as binders for coating materials, especially powder coatings, adhesives, putties or especially as thick-layer polyolefin mouldings which are in long-term contact with extractive media, such as, for example, pipes for liquids or gases, films, fibres, geomembranes, tapes, profiles or tanks.

The preferred thick-layer polyolefin mouldings have a layer thickness of from 1 to 50 mm, in particular from 1 to 30 mm, for example from 2 to 10 mm.

The compositions according to the invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, andirons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Thus, a further embodiment of the present invention relates to a shaped article, in particular a film, pipe, profile, bottle, tank or container, fiber containing a composition as described above.

A further embodiment of the present invention relates to a molded article containing a composition as described above. The molding is in particular effected by injection, blow, compression, roto-molding or slush-molding or extrusion.

The present invention also relates to compositions comprising a film forming binder and a compound of the formula I. Such compositions comprise coatings, paints, inks and adhesives. Coatings, paints and inks can be used as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of image wise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination. The quantity applied (coat thickness) and the nature of the substrate (layer support) are dependent on the desired field of application.

The present invention also relates to a process for releasing fragrances, UV absorbers, antimicrobials, anti-fogging agents and clarifiers which comprises irradiation of a photolatent compound of the formula I with light.

Preferably, the light has a wavelength of 200-700 nm, more specifically 250-400 nm.

The preferred photolatents compounds of the formula I and optionally further additives, in the process for releasing fragrances, UV absorbers, anti-microbials, anti-fogging agents and clarifiers with light are the same as those described for the new compounds of the formula I and the composition. In the context of the current invention fragrances include fragrances and flavours consciously and subconsciously perceptible by humans and animals by the sense of smell and taste including pheromones, attractants and repellants for insects, rodents and other pests and bait scents and blends thereof.

A preferred embodiment of the present invention is also the use of a photolatent compounds of the formula I as precursors for the release of fragrances, UV absorbers, anti-microbials, anti-fogging agents and clarifiers with light. A specific application for photolatent compounds for the release of fragrances are nature imitation products like synthetic wood or leather, material which is made from synthetic and natural products with the appearance and haptic qualities of wood or leather. Additionally the present invention relates to a process wherein the fragrance is released in order to conceal malodours emitted by a product.

Some of the starting materials for the preparation of the photolatent compounds of the formula I are new.

The present invention relates therefore also to new compounds of the formula Ia

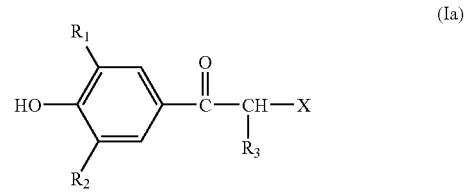

wherein $R_1$ and $R_2$ are each independently of the other $C_1$-$C_{10}$alkyl or $C_3$-$C_8$cycloalkyl, $R_3$ is hydrogen or $C_1$-$C_4$alkyl, and X is chloro, bromo or iodo; with the proviso that, when X is chloro, $R_1$ is iso-propyl, sec-butyl or cyclohexyl and $R_2$ is cyclohexyl; and with the proviso that, when X is bromo, $R_1$ and $R_2$ are cyclohexyl.

The following examples illustrate the invention further. Parts or percentages relate to weight.

EXAMPLE 1

Preparation of 1-(4-hydroxy-3,5-di-isopropylphenyl)-2-iodo-ethanone (compound 201)

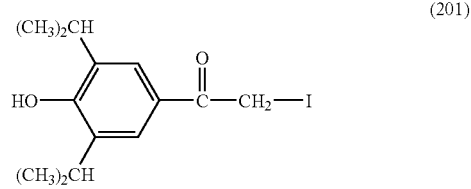

To a solution of 50.95 g (200 mmol) of 2-chloro-1-(4-hydroxy-3,5-di-isopropylphenyl)-ethanone in 250 ml of 1,2-dimethoxyethane, a solution of 30.94 g (206 mmol) of sodium iodide in 250 ml of 1,2-dimethoxyethane is added dropwise at room temperature. After the addition, stirring is continued for 16 hours at room temperature. Then 100 ml of hexane is added and, after stirring for additional 15 minutes, the precipitated salts are removed by filtration. The obtained solution is evaporated and the resulting residue is purified by recrystallization from hexane/dichloromethane to give 48.5 g (70%) of compound 201, m.p. 127-128° C.

EXAMPLE 2

Preparation of 1-(4-hydroxy-3,5-di-tert-butylphenyl)-2-iodo-ethanone (compound 202)

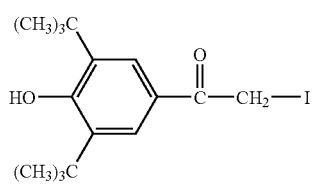
(202)

To a solution of 6.54 g (20 mmol) of 2-bromo-1-(4-hydroxy-3,5-di-tert-butylphenyl)-ethanone in 25 ml of 1,2-dimethoxyethane, a solution of 3.14 g (21 mmol) of sodium iodide in 25 ml of 1,2-dimethoxyethane is added dropwise at room temperature. After the addition, stirring is continued for 16 hours at room temperature. Then 10 ml of hexane is added and, after stirring for additional 15 minutes, the precipitated salts are removed by filtration. The obtained solution is evaporated and the resulting residue is purified by recrystallization from hexane to give 5.21 g (70%) of compound 202, m.p. 88-89° C.

EXAMPLE 3

Preparation of 1-(4-hydroxy-3,5-di-cyclohexyphenyl)-2-iodo-ethanone (compound 203)

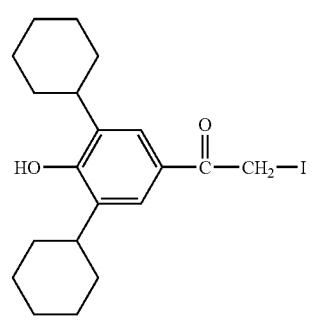
(203)

To a solution of 19.47 g (50 mmol) of 2-bromo-1-(4-hydroxy-3,5-di-cyclohexylphenyl)-ethanone in 75 ml of 1,2-dimethoxyethane, a solution of 7.87 g (50 mmol) of sodium iodide in 75 ml of 1,2-dimethoxyethane is added dropwise at room temperature. After the addition, stirring is continued for 16 hours at room temperature. Then 25 ml of hexane is added and, after stirring for additional 15 minutes, the precipitated salts are removed by filtration. The obtained solution is evaporated and the resulting residue is purified by recrystallization from hexane to give 12.1 g (57%) of compound 203, m.p. 183-185° C.

EXAMPLE 4

Preparation of 1-(3,5-bis(1,1-dimethylpropyl)-4-hydroxyphenyl)-2-iodo-ethanone (compound 204)

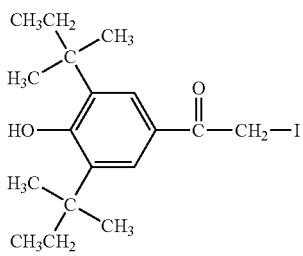
(204)

To a solution of 3.56 g (10 mmol) of 1-(3,5-bis(1,1-dimethylpropyl)-4-hydroxyphenyl)-2-bromo-ethanone in 15 ml of 1,2-dimethoxyethane, a solution of 1.65 g (11 mmol) of sodium iodide in 10 ml of 1,2-dimethoxyethane is added dropwise at room temperature. After the addition, stirring is continued for 16 hours at room temperature. Then 5 ml of hexane is added and, after stirring for additional 15 minutes, the precipitated salts are removed by filtration. The obtained solution is evaporated and the resulting residue is purified by recrystallization from hexane to give 2.15 g (53%) of compound 204, m.p. 76-77° C.

EXAMPLE 5

Preparation of 1-(4-hydroxy-3,5-tert-butylphenyl)-2-iodo-propane-1-one (compound 205)

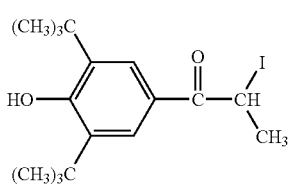
(205)

1.58 g (10.5 mmol) of sodium iodide and 3.41 g (10.0 mmol) of 2-bromo-1-(4-hydroxy-3,5-di-tert-buylphenyl)-propan-1-one is dissolved in 25 ml of 1,2-dimethoxyethane and stirred overnight at room temperature. The reaction mixture is then concentrated to two-thirds of its volume, the inorganic precipites are filtered off and washed with ethylacetate. The collected organic filtrates are washed three times with water and concentrated. The resulting residue is purified by crystallization hexane to give 2.91 g (75%) of compound 205; mp. 141° C.

EXAMPLE 6

Preparation of 4-[2-(3,5-di-tert-butyl-4-hydroxyphenyl)-2-oxo-ethoxy]-3-methoxy-benzaldehyde (compound 101)

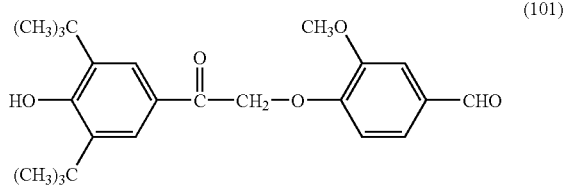

(101)

A mixture of 19.4 g (125 mmol) of 4-hydroxy-3-methoxy-benzaldehyde, 1.88 g (12.5 mmol) of sodium iodide and 34.5 g (250 mmol) of potassium carbonate in 1000 ml of ethyl acetate is stirred for 30 minutes. Then 43.6 g (125 mmol) of 2-bromo-1-(4-hydroxy-3,5-di-tert-butylphenyl)-ethanone is added and stirring at room temperature is continued for 16 hours. Then the mixture is acidified with 2N HCl and extracted with ethyl acetate. The combined extracts are washed with water, dried and evaporated. Crystallization of the crude product from dichloro-methane/hexane yields 36.85 g of compound 101, m.p. 99-100° C.

EXAMPLE 7

Preparation of 4-[2-(3,5-di-isopropyl-4-hydroxyphenyl)-2-oxo-ethoxy]-3-methoxy-benzaldehyde (compound 102)

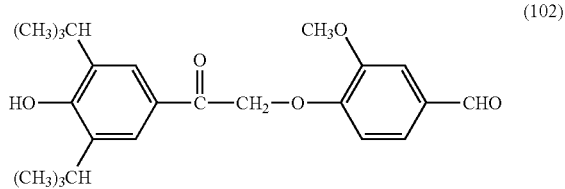

(102)

To a solution of 6.00 g (18.3 mmol) of 2-bromo-1-(4-hydroxy-3,5-di-isopropylphenyl)-ethanone and 2.78 g (18.3 mmol) of 4-hydroxy-3-methoxy-benzaldehyde in 20 ml of ethyl acetate 5.00 g (36.7 mmol) of potassium carbonate is added and the mixture is stirred for 18 hours at room temperature. After addition of water and adjusting the pH to 5-6 by adding 32% HCl, the mixture is extracted with ethyl acetate. The combined extracts are washed with water, dried and evaporated to give compound 102. $^1$H-NMR (300 MHz, CDCl$_3$), δ (ppm): 7.79 (s, 2H), 7.46-7.45 (d, 1H), 7.41-7.38 (dd, 1H), 6.90-6.87 (d, 1H), 5.43 (s, 2H), 3.97 (s, 3H), 3.24-3.15 (sept., 2H), 1.32-1.29 (d, 12H).

EXAMPLE 8

Preparation of 4-[2-(3,5-di-cyclohexyl-4-hydroxyphenyl)-2-oxo-ethoxy]-3-methoxy-benzaldehyde (compound 103)

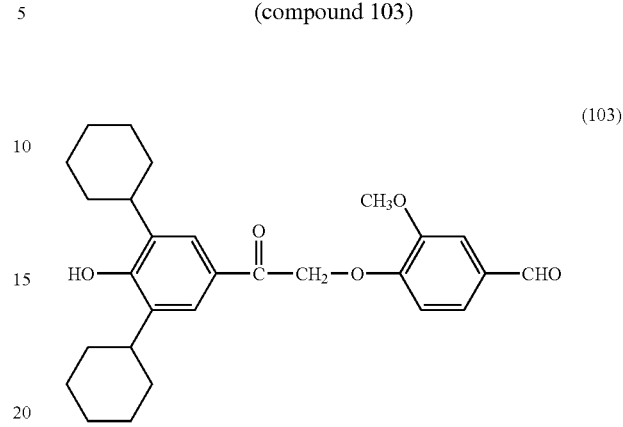

(103)

A mixture of 1.52 g (10 mmol) of 4-hydroxy-3-methoxy-benzaldehyde, 0.3 g (2.0 mmol) of sodium iodide and 3.05 g (22 mmol) of potassium carbonate in 80 ml of ethyl acetate is stirred for 30 minutes. Then 3.8 g (10 mmol) of 2-bromo-1-(4-hydroxy-3,5-di-cyclohexylphenyl)-ethanone is added and stirring at room temperature is continued for 16 hours. Then the mixture is acidified with 2N HCl and extracted with ethyl acetate. The combined extracts are washed with water, dried and evaporated. Crystallization of the crude product from dichloro-methane/di-isopropylether yields 1.35 g of compound 103, m.p. 163-164° C.

EXAMPLE 9

Preparation of 2-[4-chloro-2-(2,4-dichloro-phenoxy)-phenoxy]-1-(3,5-di-tert-butyl-4-hydroxyphenyl)-ethanone (compound 104)

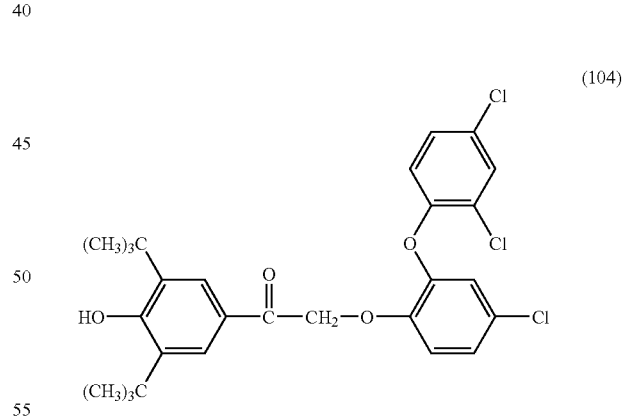

(104)

To a solution of 10.0 g (30.5 mmol) of 2-bromo-1-(4-hydroxy-3,5-di-tert-butylphenyl)-ethanone and the 8.8 g (30.5 mmol) of 5-chloro-2-(2,4-di-chloro-phenoxy)-phenol in 50 ml of tetrahydrofuran, 6.3 g (45.7 mmol) of potassium carbonate is added and the mixture is stirred for 4 days at room temperature. After addition of water and adjusting the pH to 5-6 by adding 32% HCl, the mixture is extracted with ethyl acetate. The combined extracts are washed with water, dried and evaporated. Crystallization of the crude product from methanol gives 15.4 g of compound 104, m.p. 111-114° C.

EXAMPLE 10

Preparation of 1-(4-hydroxy-3,5-di-isopropylphenyl)-2-p-tolyloxy-ethanone (compound 105)

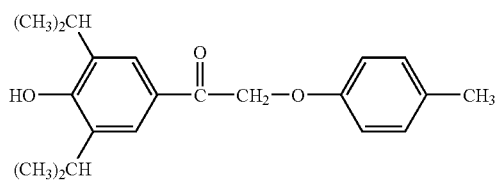

(105)

To a solution of 4.47 g (30.6 mmol) of potassium 4-methylphenolate in 150 ml of dimethyl-formamide a solution of 3.90 g (15.3 mmol) of 2-chloro-1-(4-hydroxy-3,5-di-isopropylphenyl)-ethanone in 70 ml dimethylformamide is added at room temperature within a period of 100 minutes. After additional 2 hours of stirring at room temperature the pH is adjusted to 6-7 with 1 N HCl and the mixture is extracted with ethyl acetate. The collected organic phases are washed with water, dried and evaporated. Crystallization of the crude product from ethyl acetate/hexane gives 1.8 g of compound 105, m.p. 124-125° C.

EXAMPLE 11

Preparation of 2-(2-benzotriazol-2-yl-4-methyl-phenoxy)-1-(3,5-di-tert-butyl-4-hydroxy-phenyl)-ethanone (compound 106)

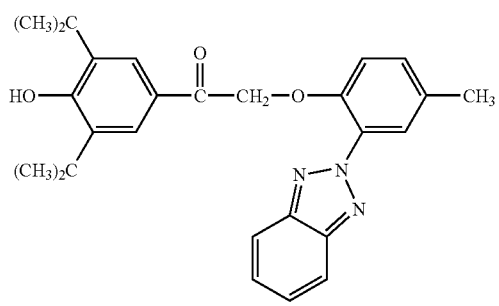

(106)

6.54 g (20 mmol) of 2-bromo-1-(4-hydroxy-3,5-di-tert-butylphenyl)-ethanone and 1.98 g (30 mmol) of potassium hydroxide are dissolved in 150 ml of acetonitrile and stirred under inert atmosphere at room temperature for 30 minutes. Then 5.27 g (20 mmol) of 2-benzotriazol-2-yl-4-methyl-phenolate is added in portions. Stirring at room temperature is continued for additional 3 hours. After adjusting the pH to 6-7 the mixture is extracted with ethyl acetate. The collected organic phases are washed with water, dried and evaporated. Crystallization of the crude product from methanol gives 6.85 g of compound 106, m.p. 155-157° C.

EXAMPLE 12

Preparation of 4-{2-[3,5-bis(1,1-dimethyl-propyl)-4-hydroxy-phenyl]-2-oxo-ethoxy}-3-methoxy-benzaldehyde (compound 107)

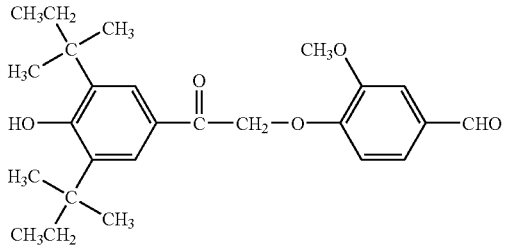

(107)

A mixture of 1.55 g (10 mmol) of 4-hydroxy-3-methoxy-benzaldehyde, 0.30 g (2.0 mmol) of sodium iodide and 3.05 g (22 mmol) of potassium carbonate in 100 ml of ethyl acetate is stirred for 30 minutes. Then 3.56 g (10 mmol) of 1-[3,5-bis(1,1-dimethyl-propyl)-4-hydroxy-phenyl]-2-bromo-ethanone is added and stirring at room temperature is continued for 16 hours. Then the mixture is acidified with 2N HCl and extracted with ethyl acetate. The combined extracts are washed with water, dried and evaporated. Crystallization of the crude product from hexane yields 2.95 g (69%) of compound 107, m.p. 106-107° C.

EXAMPLE 13

Preparation of 2-[(E)-3,7-dimethyl-octa-2,6-dienyloxy]-1-(4-hydroxy-3,5-di-isopropyl-phenyl)-ethanone (compound 108)

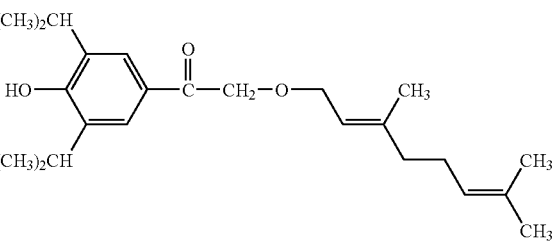

(108)

To a solution of 86.4 g (560 mmol) of (E)-3,7-dimethyl-octa-2,6-dien-1-ol and 64.5 g (1150 mmol) of potassium hydroxide in 150 ml of N-methylpyrrolidone a solution of 58.59 g (230 mmol) of 2-chloro-1-(4-hydroxy-3,5-di-isopropylphenyl)-ethanone in 100 ml of N-methylpyrrolidone is added dropwise at room temperature and under inert atmosphere. After the addition is completed stirring is continued for additional 16 hours. Then the reaction mixture is acidified with 1N HCl and extracted with ethyl acetate. The collected organic phases are washed with water and brine, dried and evaporated. Crystallization of the crude product from hexane gives 45.3 g of compound 108, m.p. 70-71° C.

EXAMPLE 14

Preparation of 2-(3,7-dimethyl-oct-6-enyloxy]-1-(4-hydroxy-3,5-di-isopropyl-phenyl)-ethanone (compound 109)

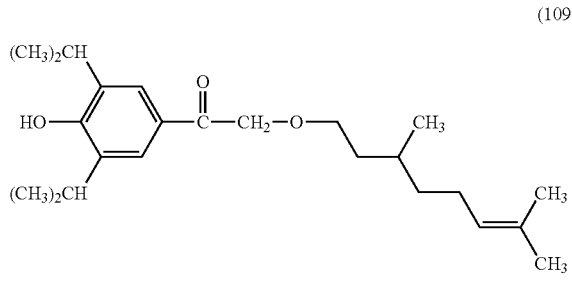

To a solution of 4.69 g (30 mmol) of 3,7-dimethyl-oct-6-dien-1-ol and 4.21 g (75 mmol) of potassium hydroxide in 150 ml of N-methylpyrrolidone a solution of 3.82 g (15 mmol) of 2-chloro-1-(4-hydroxy-3,5-di-isopropylphenyl)-ethanone in 75 ml of N-methylpyrrolidone is added dropwise at room temperature and under inert atmosphere. After the addition is completed stirring is continued for additional 16 hours. Then the reaction mixture is acidified with 1N HCl and extracted with ethyl acetate. The collected organic phases are washed with water and brine, dried and evaporated. Crystallization of the crude product from hexane gives 2.58 g of compound 109, m.p. 37-39° C.

EXAMPLE 15

Preparation of 1-(4-hydroxy-3,5-di-isopropylphenyl)-2-[(1R,2S,5R)-2-isopropyl-5-methyl-cyclohexyloxy]-ethanone (compound 110)

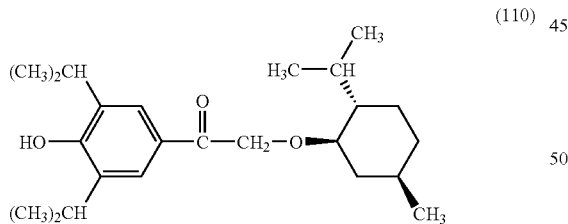

To a solution of 15.63 g (100 mmol) of (1R,2S,5R)-2-isopropyl-5-methyl-cyclohexanol and 16.5 g (250 mmol) of potassium hydroxide in 100 ml of N-methylpyrrolidone a solution of 12.73 g (50 mmol) of 2-chloro-1-(4-hydroxy-3,5-di-isopropylphenyl)-ethanone in 400 ml of N-methylpyrrolidone is added dropwise at room temperature and under inert atmosphere. After the addition is completed stirring is continued for additional 16 hours. Then the reaction mixture is acidified with 1N HCl and extracted with ethyl acetate. The collected organic phases are washed with water and brine, dried and evaporated. Crystallization of the crude product from hexane gives 6.37 g of compound 110, m.p. 83-84° C.

EXAMPLE 16

Preparation of 2-(1,5-dimethyl-1-vinyl-hex-4-enyloxy)-1-(4-hydroxy-3,5-diisopropylphenyl)-ethanone (compound III)

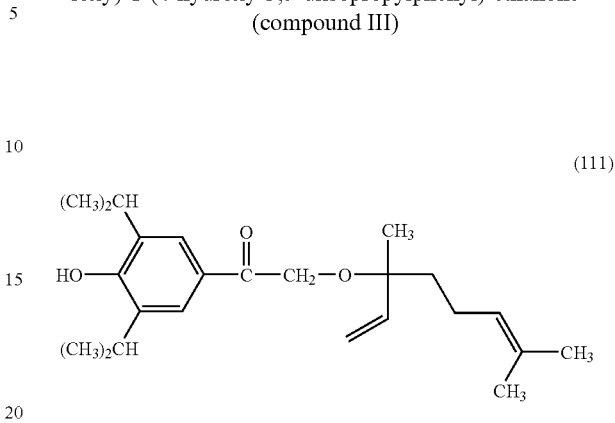

To a solution of 12.7 g (79 mmol) of 3,7-dimethyl-octa-1,6-dien-3-ol and 10.9 g (195 mmol) of potassium hydroxide in 80 ml of N-methylpyrrolidone a solution of 10.0 g (39 mmol) of 2-chloro-1-(4-hydroxy-3,5-di-isopropylphenyl)-ethanone in 120 ml of N-methylpyrrolidone is added dropwise at room temperature and under inert atmosphere. After the addition is completed stirring is continued for additional 16 hours. Then the reaction mixture is acidified with 1N HCl and extracted with ethyl acetate. The collected organic phases are washed with water and brine, dried and evaporated. Crystallization of the crude product from hexane gives 0.32 g of compound III, m.p. 71-72° C.

EXAMPLE 17

Preparation of 2-ethoxy-1-(4-hydroxy-3,5-di-is-propyl-phenyl)-ethanone (compound 112)

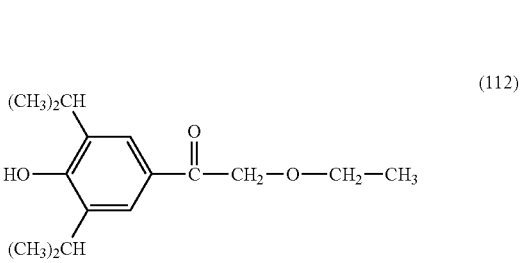

Under inert atmosphere 187 g (3.33 mol) of potassium hydroxide is dissolved in 1000 ml of ethanol. After adding 254.8 g (1.00 mol) of 2-chloro-1-(4-hydroxy-3,5-di-isopropylphenyl)-ethanone in portions at room temperature stirring is continued for 16 hours. Then the reaction mixture is acidified with 10% HCl and extracted with ethylacetate. The collected organic phases are washed with water and brine, dried and evaporated. Crystallization of the crude product from toluene/hexane and isopropanol/water gives 243 g of compound 112, m.p. 97-98° C.

EXAMPLE 18

Preparation of 2-ethoxy-1-(4-hydroxy-3,5-di-tert-butylphenyl)-ethanone (compound 113)

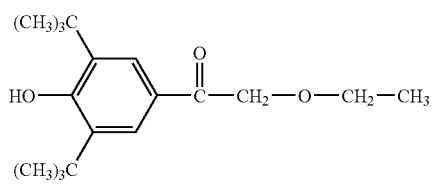

(113)

Under inert atmosphere 8.4 g (150 mmol) of potassium hydroxide is dissolved in 150 ml of ethanol. After adding 10.0 g (31 mmol) of 2-bromo-1-(4-hydroxy-3,5-di-tert-butylphenyl)-ethanone in portions at room temperature stirring is continued for 16 hours. Then the reaction mixture is acidified with 10% HCl and extracted with ethylacetate. The collected organic phases are washed with water and brine, dried and evaporated. Crystallization of the crude product from hexane gives 3.8 g of compound 113, m.p. 73-75° C.

EXAMPLE 19

Preparation of 2-[2-(4-hydroxy-3,5-di-isopropylphenyl)-2-oxo-ethoxy]-isoindole-1,3-dione (compound 114)

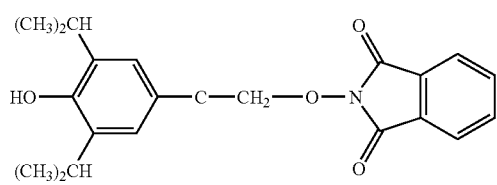

(114)

A mixture of 3.03 g (15 mmol) of potassium 1,3-dioxo-1,3-dihydro-isoindol-2-olate [prepared according to P. Consonni, D Favara, A. Omodei-Salé, G. Bartolini, A. Ricci, *J. Chem. Soc.*, Perkin Trans. 2, 1983, 967-973], 3.82 g (15 mmol) of 2-chloro-1-(4-hydroxy-3,5-di-iso-propyl-phenyl)-ethanone, 2.3 ml of triethylamine and 100 ml of dimethylformamide is stirred at room temperature and under nitrogen atmosphere for 1.5 hours. Then the mixture is poured onto 500 ml of water containing 9 ml of 2N HCl and is extracted with ethyl acetate. The collected organic phases are washed with water, dried and evaporated. The resulting crude product is recrystallized from ethyl acetate and hexane to give 2.52 g of compound 114, m.p. 136-139°.

EXAMPLE 20

Preparation of 1-(3,5-di-tert-butyl-4-hydroxyphenyl)-2-ethoxy-propan-1-one (compound 115)

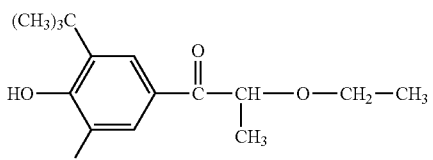

(115)

6.6 g (117 mmol) of potassium hydroxide are dissolved in 130 ml of ethanol and stirred for one hour. Then 10.0 g (29.3 mmol) of 2-bromo-1-(3,5-di-tert-butyl-4-hydroxyphenyl)-propan-1-one dissolved in 20 ml of n-methylpyrrolidone is added at room temperature while stirring. After stirring for 20 hours the reaction mixture is cooled with an ice bath and 5 ml of concentrated hydrochloric acid and 150 ml of water is added. Then ethanol is evaporated, 200 ml of ethylacetate added and the water phase split off. The organic phase is washed with 100 ml of brine, dried over sodium sulfate and evaporated. The residue is purified by column chromatography and crystallisation of the pure fractions from hexane to give 4.1 g (45%) of compound 115; m.p. 64° C.

EXAMPLE 21

Preparation of 1-(3,5-di-tert-butyl-4-hydroxyphenyl)-2-[(E)-3,7-dimethyl-octa-2,6-dienyloxy]-ethanone (compound 116)

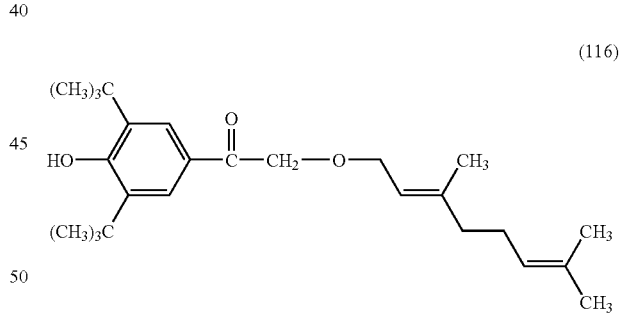

(116)

A mixture of 9.6 g (62 mmol) of (E)-3,7-dimethyl-octa-2,6-dien-1-ol, 8.4 g (150 mmol) of potassium hydroxide and 20 ml of n-methylpyrrolidone are stirred for one hour at room temperature. Then 10.0 g (33 mmol) of 2-bromo-1-(3,5-di-tert-butyl-4-hydroxyphenyl)-ethanone is added in portions and stirring is continued at room temperature for 20 hours. After the addition of 30 ml of water the mixture is neutralized with 6N hydrochloric acid while cooling with an ice bath and then extracted with ethyl acetate. The organic phases are washed twice with brine, dried over sodium sulfate and evaporated. The residue is purified by column chromatography and crystallisation of the pure fractions from hexane gives 6.1 g (50%) of compound 116; m.p. 50° C.

EXAMPLE 22

Preparation of 2-(2-benzotriazol-2-yl-4-methyl-phenoxy)-1-(3,5-di-tert-butyl-4-hydroxy-phenyl)-propan-1-one (compound 117)

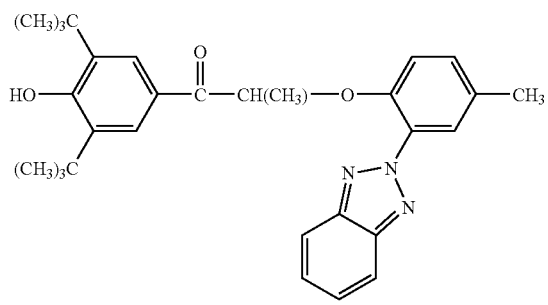
(117)

A mixture of 5.5 g (24 mmol) of 2-benzotriazol-2-yl-4-methyl-phenol, 4.7 g (72 mmol) of potassium hydroxide and 100 ml of n-methylpyrrolidone is stirred for 2 hours at room temperature. Then 8.0 g (24 mmol) 2-bromo-1-(3,5-di-tert-butyl-4-hydroxyphenyl)-propan-1-one dissolved in 40 ml of n-methylpyrrolidone is added and stirring is continued at room temperature for 20 hours. After the addition of 50 ml of water and 15 ml 2N hydrochloric acid the precipitated solid is filtered off and recrystallized from ethanol to give 8.9 g (76%) of compound 117; m.p. 161° C.

EXAMPLE 23

Photochemical Release of Vanilla in Polypropylene 0.50 g Irganox® B 215 [Ciba Specialty Chemicals Inc.; a mixture of one part Irganox® 1010 (pentaerythritol ester of 3-(3,5-di-tert-butyl-4-hydroxyphenyl)propionic acid) and two parts Irgafos® 168 (tris(2,4-di-tert-butylphenyl)phosphite)] and 30 g of compound (101) [prepared according to Example 6] are mixed in a turbo mixer with 969.5 g of polypropylene powder Profax PH 350 from Basell. The mixture is extruded at 160-170° C. in a twin screw extruder producing tapes with a width of 20 mm and a thickness of 1 mm. The tapes are cut into pieces with a length of about 50 mm and irradiated on PPG UV-curing equipment using 2 Hg-arc bulbs at 80 W/cm and a line speed of 20 m/min. The irradiation is repeated until the number of passages under the lamp indicated in Table 1 is reached. The release of vanilla from the samples is detected by smelling the surface and the strength of the vanilla smell is categorized into the following:

| No vanilla smell | – |
| Very slight hint of vanilla smell | (+) |
| Weak vanilla smell | + |
| Significant vanilla smell | ++ |
| Strong vanilla smell | +++ |

The results are summarized in Table 1.

TABLE 4

| Example | Number of passages under the lamp | Vanilla smell |
| --- | --- | --- |
| 23a | 0 | (+) |
| 23b | 2 | (+) |
| 23c | 5 | + |
| 23d | 10 | +++ |

EXAMPLE 24

Photochemical Fragrance Release from Coatings

Parts and percentages are by weight, unless stated otherwise.

The following photolatent fragrances are used: compound 101 [photolatent vanillin]; compound 108 [photolatent geraniol]; compound 109 [photolatent citronellol] and compound 110 [photolatent menthol].

The scent is evaluated olfactorily by at least 2 persons. The strength of perception is ranked in 3 categories:

| no smell | – |
| weak smell | + |
| strong smell | ++ |

EXAMPLE 24.1

Photochemical Release of Fragrances from Conventional Clear Coat

A clear solvent borne thermo setting coating is prepared according to following formulation according to Table 2:

TABLE 2

| Product | Description | Supplier | Parts (%) Millibase | Parts (%) Let-Down |
| --- | --- | --- | --- | --- |
| 1-Butanol | Solvent | | 4.00 | 5.14 |
| Baysilone MA (100%) | Antisettling and Flow Additive | Borchers GmbH | 0.035 | 0.045 |
| Butylglycolacetate | Solvent | | 4.00 | 2.57 |
| Setal 84xx-70 (70%) | Short Oil Alkyd Resin | Nuplex Resins | 42.93 | 55.06 |
| Setamine US 138BB70 (70%) | Butylated Melamine Formaldehyd Resin | Nuplex Resins | 16.66 | 21.39 |
| Solvesso 100 | Solvent | | 32.36 | 15.79 |

The final formulation is prepared by mixing Millbase and Let-Down in a ratio of Millbase:Let-Down=30:70. The following samples are prepared (Table 3):

TABLE 3

| Example | Photolatent Fragrance | Weight [g/100 g Formulation] |
| --- | --- | --- |
| 24a | none | none |
| 24b | Compound 101 | 1.40 |
| 24c | Compound 108 | 1.40 |

TABLE 3-continued

| Example | Photolatent Fragrance | Weight [g/100 g Formulation] |
|---|---|---|
| 24d | Compound 109 | 1.40 |
| 24e | Compound 110 | 1.40 |

The photolatent fragrances are dissolved in the formulation at a concentration of 7.5 mmol on 100 g solids. Samples of 20 g liquid formulation are prepared by dissolving the photolatent fragrance in the formulation by stirring at room temperature. Samples are applied on white pre-coated aluminum panels using a wire-wound draw-down bar at a wet film thickness of 200 μm and cured in a convection oven at 120° C. for 30 min. The fragrance of the samples are then evaluated before and after irradiation on UV-curing equipment GEO UV Processor by AETEC International using 2 Hg-medium pressure lamps at 80 W/cm and a line speed of 10 m/min. The olfactory evaluation before and after curing is summarized in Table 4.

TABLE 4

| Example | Fragrance before Irradiation | Fragrance after Irradiation | Description of Fragrance |
|---|---|---|---|
| 24a | none | none | No fragrance |
| 24b | none | ++ | Vanilla like |
| 24c | none | + | Fruity, floral, fresh |
| 24d | none | ++ | Fresh, citrus like |
| 24e | none | ++ | Fresh, minty |

EXAMPLE 24.2

Photochemical Release of Fragrances from Aqueous Clear Coat

A water thinnable clear coating is prepared according to following formulation according to Table 5:

TABLE 5

| Product | Description | Supplier | Parts (%) |
|---|---|---|---|
| Water demineralized | Solvent | | 47.0 |
| Maprenal MF 900W/95 | Melamine-formaldehyde resin | Cytec Surface Specalties | 0.54 |
| Surfynol 104E | Nonionic wetting and foam control additive | Air Products | 0.8 |
| Surfynol MD20 | Foam control and wetting additive | Air Products | 0.3 |
| EnviroGem AE02 | Wetting Agent | Air Products | 0.4 |
| Butyl glycol | Solvent | | 5.51 |
| n-Butanol | Solvent | | 2.0 |
| Dow Corning 57 | Slip Additive | Dow Corning | 0.2 |
| Viscalex HV30 | Thickener and rheology control additive | Ciba Specialty Chemicals | 3.5 |
| DMEA (10% in water) | Dimethylaminoethanol | Fluka | 2.5 |
| APU 1012 | Aqueous acrylic polyurethane dispersion | Alberdingk Boley | 37.25 |

The following samples are prepared (Table 6):

TABLE 6

| Example | Photolatent Fragrance | Weight [g/100 g Formulation] |
|---|---|---|
| 24f | none | none |
| 24g | Compound 101 | 0.534 |

TABLE 6-continued

| Example | Photolatent Fragrance | Weight [g/100 g Formulation] |
|---|---|---|
| 24h | Compound 108 | 0.534 |
| 24i | Compound 109 | 0.534 |
| 24j | Compound 110 | 0.534 |

The quantity of photolatent fragrance equals an amount of 3% on solids. Samples are pre-pared by stirring 60 minutes at 40° C. All photolatent fragrances are soluble in the aqueous formulation. Coating is applied onto white pre-coated aluminum panels using a wire-wound draw down bar with a wet film thickness of 150 μm. Samples are then dried in a convection oven for 30 min at 130° C. Panels are cut into 2 pieces. One set of samples is irradiated on UV-curing equipment as described in Example 24.1. The fragrance is evaluated before and after irradiation. The results of olfactory evaluation of fragrance strength are shown in the following Table 7.

TABLE 7

| Example | Fragrance before Irradiation | Irradiation on UV-curing equipment | Description of Fragrance |
|---|---|---|---|
| 24f | none | None | No fragrance |
| 24g | none | 2 | Vanilla like |
| 24h | none | + | Fruity, floral, fresh |
| 24i | none | ++ | Fresh, citrus like |
| 24j | none | ++ | Fresh, minty |

EXAMPLE 24.3

Photochemical Release of Vanilla in Pigmented Conventional Coating

A white thermosetting screening formulation is prepared based on an alkyd/melamin system with the following ingredients:

1. Millbase: (Table 8)

TABLE 8

| Product | Description | Supplier | Parts |
|---|---|---|---|
| Alkydal F 310 (60%) | Short-oil alkyd resin Based on saturated fatty acids | Bayer Material Science | 27.58 |
| Disperbyk 161 | High molecular weight Wetting and dispersing Additive for solvent-Based coatings | BYK Chemie | 5.5 |
| Silicone oil (1% in xylol) | | | 1.0 |
| 1-Methoxy-2-propanol | Solvent | | 1.56 |
| Butanol | Solvent | | 1.56 |
| Xylol | Solvent | | 7.3 |
| Aerosil 200 | Hydrophilic fumed silica | Degussa | 0.5 |
| Tiona 696 | Rutile pigment | Millennium Chemicals | 55.0 |
| Sum | | | 100.0 |

2. Let-Down: (Table 9)

TABLE 9

| Product | Description | Supplier | Parts |
|---|---|---|---|
| Millbase | see Table 1 | | 45.45 |
| Alkydal F 310 (60%) | Short-oil alkyd resin Based on saturated fatty acids | Bayer Material Science | 35.08 |
| Maprenal MF 650 | Melamine resin | Cytec Surface Specialties | 17.59 |
| 1-Methoxy-2-propanol | Solvent | | 0.22 |
| Butanol | Solvent | | 0.22 |
| Xylol | Solvent | | 1.04 |
| Tinuvin 123 | Light stabilizer | Ciba Specialty Chemicals | 0.40 |
| Sum | | | 100.0 |

Pigment loading is 25%.

Sample Preparation [Example 24I]: 1.147 g of compound 101 [see Example 6] is weighed on 100 g of screening formulation resulting in a content of photolatent substance of 3% on solids. The sample is stirred at 50° C. for approximately 60 minutes on a magnet stirring device.

Samples are applied over aluminium panels with white coil coating primer using a wire-coater (WFT 100 μm) and cured in oven at 130° C. for 40 minutes. For reference a sample of the pure screening formulation is applied as described before [Example 24k].

Irradiation and Release of Vanilla

1. Irradiation with UV-Curing Equipment:

The cured samples were irradiated on PPG UV-curing equipment as described in Example 24.1. using 2 Hg-arc bulbs at 80 W/cm and a line speed of 10 m/minutes immediately after UV-irradiation. The release of vanilla from the samples is detected by smelling the surface of the coating. The results are summarized in Table 10.

TABLE 10

| Example | Photolatent compound | Vanilla smell |
|---|---|---|
| 24k[a)] | none | none |
| 24l[b)] | 3% of compound 101 | ++ |

[a)]Comparison Example.
[b)]Example according to the invention.

2. Irradiation with Artificial Daylight

Samples are placed underneath an artificial daylight lamp according to DIN 6173 and irradiated during 4 working weeks (5 days/week) with an interruption of 2 days between the weeks, where samples are stored in a dark place. In intervals, the release of vanilla from the samples is detected by smelling the surface of the coatings. The strength of vanilla smell is evaluated as described before. The results are summarized below:

| | Week 1 | | | | Week 2 | | |
|---|---|---|---|---|---|---|---|
| Example | 5 h | 24 h | 48 h | 72 h | 96 h | 24 h | 48 h | 96 h |
| 24k | − | − | − | − | − | − | − | − |
| 24l | + | ++ | ++ | ++ | ++ | ++ | ++ | ++ |

| | Week 3 | Week 4 | |
|---|---|---|---|
| Example | 48 h | 48 h | 96 h |
| 24l | ++ | + | − |

EXAMPLE 24.4

Photochemical Release of Fragrances in Combination with Photosensitizers in Conventional Clear Coat The coatings formulation used in this Example equals the one described in Example 24.1. The following samples are prepared (Table 11):

TABLE 11

| Example | Photolatent Fragrance | Photosensitizer |
|---|---|---|
| 24m | Compound 108 | Blend of 2-isopropylthioxanthone and 4-isopropylthioxanthone (Darocur ITX) |
| 24n | Compound 108 | 1-chloro-4-propoxy-9H-thioxanthene-9-one (Aldrich) |
| 24o | Compound 108 | Benzophenone (Darocur BP) |
| 24p | Compound 110 | Blend of 2-isopropylthioxanthone and 4-isopropylthioxanthone (Darocur ITX) |
| 24q | Compound 110 | 1-chloro-4-propoxy-9H-thioxanthene-9-one (Aldrich) |
| 24r | Compound 110 | Benzophenone (Darocur BP) |

The samples contain 1.5 g (3% on solids) of photolatent fragrance and 1.0 g (2% on solids) of photosensitizer on 100 g formulation. Both additives are added to the coating and are dissolved by stirring at 40° C. Samples are applied on white pre-coated aluminium panels using a wire-wound draw down bar with a wet film thickness of 120 μm and cured in a convection oven for 30 min at 100° C. The coated panels are cut into smaller pieces for irradiation under UV-fluorescent lamps TL K 40 W/05 (Philips, emission peak at 365 nm) for about 30 minutes and with natural daylight, summer, afternoon, southside, closed cloud layer for about 60 minutes. The results of fragrance strength are shown below in Table 12.

TABLE 12

| Example | Fragrance before Irradiation | Fragrance with UV-fluorescent lamps | Fragrance with Natural daylight |
|---|---|---|---|
| 24m | none | + | + |
| 24n | none | + | + |
| 24o | none | + | + |
| 24p | none | + | + |
| 24q | none | + | + |
| 24r | none | + | + |

What is claimed is:

1. A photolatent compound of the formula I

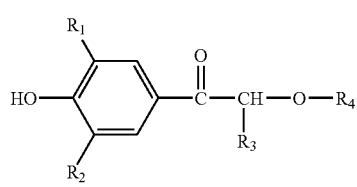

wherein $R_1$ and $R_2$ are each independently of the other $C_1$-$C_{10}$alkyl or $C_3$-$C_8$cycloalkyl, $R_3$ is hydrogen or $C_1$-$C_4$alkyl, and $R_4$ is unsubstituted $C_1$-$C_{25}$alkyl, $C_3$-$C_{25}$alkenyl, $C_3$-$C_{25}$alkinyl, $C_6$-$C_{10}$aryl, $C_3$-$C_{12}$cycloalkyl or $C_3$-$C_{12}$cycloalkenyl; or is $C_1$-$C_{25}$alkyl, $C_3$-$C_{25}$alkenyl, $C_3$-$C_{25}$alkinyl, $C_6$-$C_{10}$aryl, $C_3$-$C_{12}$cycloalkyl or $C_3$-$C_{12}$cycloalkenyl substituted with $C_1$-$C_{18}$alkyl, $C_2$-$C_{18}$alkenyl, $C_3$-$C_{18}$alkinyl, $C_3$-$C_{12}$cycloalkyl, $C_1$-$C_{18}$alkoxy, hydroxyl, $C_2$-$C_{18}$alkoxycarbonyl, formyl, $C_1$-$C_{18}$alkylthio, $C_1$-$C_{18}$alkylsulfinyl, $C_1$-$C_{18}$alkylsulfonyl, halogen, carboxy, $C_2$-$C_{18}$carboxyalkyl, $C_2$-$C_{18}$carboxyalkoxy, $C_3$-$C_{18}$-alkoxycarbonylalkyl, $C_3$-$C_{18}$-alkoxycarbonylalkoxy, $C_7$-$C_9$phenylalkyl, phenoxy, halogen substituted phenoxy,

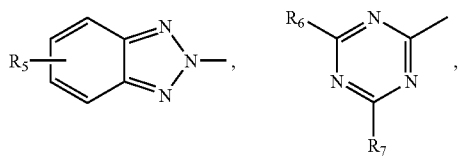

sorbityl or

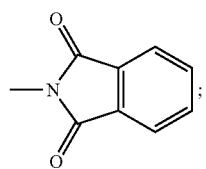

$R_5$ is hydrogen, $C_1$-$C_4$alkyl or halogen, and $R_6$ and $R_7$ independently of each other are phenyl or $C_1$-$C_4$alkyl substituted phenyl; and with the proviso that, when $R_1$ and $R_2$ are tert-butyl and $R_3$ is hydrogen, $R_4$ is not methyl or phenyl.

2. A photolatent compound according to claim 1, wherein $R_1$ and $R_2$ are each independently of the other $C_3$-$C_8$alkyl or $C_5$-$C_8$cycloalkyl, $R_3$ is hydrogen or methyl, $R_4$ is unsubstituted $C_1$-$C_{18}$alkyl, $C_3$-$C_{18}$alkenyl, $C_3$-$C_{18}$alkinyl, $C_6$-$C_{10}$aryl, $C_5$-$C_8$cycloalkyl or $C_5$-$C_8$cycloalkenyl; or $C_1$-$C_{18}$alkyl, $C_3$-$C_{18}$alkenyl, $C_3$-$C_{18}$alkinyl, $C_6$-$C_{10}$aryl, $C_5$-$C_8$cycloalkyl or $C_5$-$C_8$cycloalkenyl substituted with $C_1$-$C_{12}$alkyl, $C_2$-$C_{12}$alkenyl, $C_3$-$C_{12}$alkinyl, $C_5$-$C_8$cycloalkyl, $C_1$-$C_{12}$alkoxy, hydroxyl, $C_2$-$C_{12}$alkoxycarbonyl, formyl, $C_1$-$C_{12}$alkylthio, $C_1$-$C_{12}$alkylsulfinyl, $C_1$-$C_{12}$alkylsulfonyl, halogen, carboxy, $C_2$-$C_{12}$carboxyalkyl, $C_2$-$C_{12}$carboxyalkoxy, $C_3$-$C_{12}$-alkoxycarbonylalkyl, $C_3$-$C_{12}$alkoxycarbonylalkoxy, $C_7$-$C_9$phenylalkyl, phenoxy, halogen substituted phenoxy,

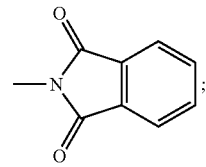

sorbityl or

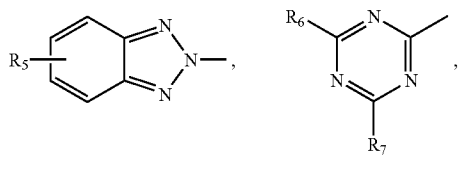

$R_5$ is hydrogen or halogen, and $R_6$ and $R_7$ are phenyl.

3. A photolatent compound according to claim 1, wherein $R_3$ is hydrogen.

4. A photolatent compound according to claim 1, wherein $R_1$ and $R_2$ are each independently of the other $C_3$-$C_5$alkyl or cyclohexyl.

5. A photolatent compound according to claim 1, wherein $R_4$ is unsubstituted $C_2$-$C_{12}$alkyl, $C_3$-$C_{12}$alkenyl, $C_3$-$C_{12}$alkinyl, phenyl, cyclohexyl or cyclohexenyl; or $C_2$-$C_{12}$alkyl, $C_3$-$C_{12}$alkenyl, $C_3$-$C_{12}$alkinyl, phenyl, cyclohexyl or cyclohexenyl substituted with $C_1$-$C_4$alkyl, $C_2$-$C_8$alkenyl, $C_3$-$C_8$alkinyl, cyclohexyl, $C_1$-$C_5$alkoxy, formyl, chloro, carboxy, $C_7$-$C_9$phenylalkyl, phenoxy, chloro substituted phenoxy,

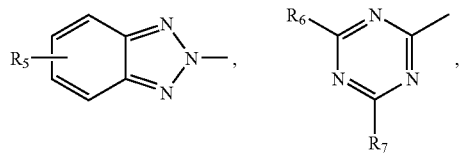

sorbityl or

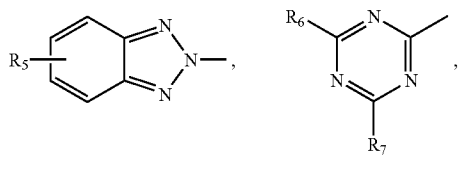

$R_5$ is hydrogen or chloro, and $R_6$ and $R_7$ are phenyl.

6. A photolatent compound according to claim 1, wherein $R_1$ and $R_2$ are isopropyl, tert-butyl, cumyl or cyclohexyl.

7. A photolatent compound according to claim 1, wherein $R_1$ is $C_3$-$C_5$alkyl or cyclohexyl, $R_2$ is $C_3$-$C_5$alkyl or cyclohexyl, $R_3$ is hydrogen, $R_4$ is unsubstituted $C_2$-$C_{12}$alkyl, $C_3$-$C_{12}$alkenyl, $C_3$-$C_{12}$alkinyl, phenyl, cyclohexyl or cyclohexenyl; or $C_2$-$C_{12}$alkyl, $C_3$-$C_{12}$alkenyl, $C_3$-$C_{12}$alkinyl, phenyl, cyclohexy or cyclohexenyl substituted with $C_1$-$C_4$alkyl, $C_2$-$C_8$alkenyl, $C_3$-$C_8$alkinyl, cyclohexyl, $C_1$-$C_8$alkoxy, formyl, chloro, carboxy,

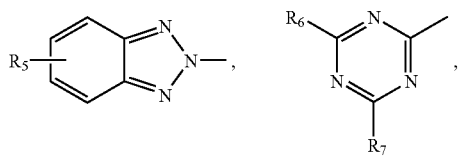 , 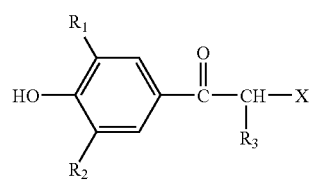 , $C_7$-$C_9$phenylalkyl, phenoxy, chloro substituted phenoxy, sorbityl or

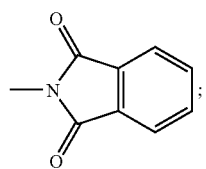 ;

$R_5$ is hydrogen or chloro, and
$R_6$ and $R_7$ are phenyl.

8. A composition comprising
a) a technical material, and
b) a photolatent compound of the formula I according to claim 1.

9. A composition according to claim 8, wherein component (b) is present in an amount of from 0.001 to 10%, based on the weight of component (a).

10. A composition according to claim 8, wherein component (a) is a solvent, a wax, a film-forming binder, a paint, a coating, a natural or synthetic polymer, a fabric, a paper, a cleaner, a polish, a fabric care, a shampoo, a hair conditioner, a hair spray, a soap, a bath or shower gel or a body deodorant.

11. A composition according to claim 8, comprising in addition to components (a) and (b), further additives.

12. A composition according to claim 11, where the further additives are phenolic antioxidants, light-stabilizers or processing stabilizers.

13. A process for releasing fragrances, UV absorbers, antimicrobials, anti-fogging agents or clarifiers, which process comprises irradation of a photolatent compound of the formula I according to claim 1 with light.

14. A process according to claim 13, wherein the light has a wavelength of 250-400 nm.

15. A compound of the formula Ia (Ia)

wherein
$R_1$ and $R_2$ are each independently of the other $C_1$-$C_{10}$alkyl or $C_3$-$C_8$cycloalkyl,
$R_3$ is hydrogen or $C_1$-$C_4$alkyl, and
X is chloro, bromo or iodo;
with the proviso that, when X is chloro, $R_1$ is iso-propyl, sec-butyl or cyclohexyl and $R_2$ is cyclohexyl; and with the proviso that, when X is bromo, $R_1$ and $R_2$ are cyclohexyl.

* * * * *